(12) United States Patent
Han et al.

(10) Patent No.: US 11,161,797 B1
(45) Date of Patent: Nov. 2, 2021

(54) PROCESS FOR PREPARING CATALYST FOR SELECTIVE HYDROGENATION OF ACETYLENE TO ETHYLENE

(71) Applicant: Taizhou University, Taizhou (CN)

(72) Inventors: Deman Han, Taizhou (CN); Rongrong Li, Taizhou (CN)

(73) Assignee: Taizhou University, Taizhou (CN)

( * ) Notice: Subject to any disclaimer, the term of this patent is extended or adjusted under 35 U.S.C. 154(b) by 0 days.

(21) Appl. No.: 16/883,502

(22) Filed: May 26, 2020

(51) Int. Cl.
*C07C 5/09* (2006.01)
*B01J 37/04* (2006.01)
*B01J 37/18* (2006.01)
*B01J 37/08* (2006.01)
*B01J 37/03* (2006.01)
*B01J 37/16* (2006.01)
*B01J 21/08* (2006.01)
*B01J 23/66* (2006.01)
*B01J 35/02* (2006.01)

(52) U.S. Cl.
CPC ............. *C07C 5/09* (2013.01); *B01J 21/08* (2013.01); *B01J 23/66* (2013.01); *B01J 35/023* (2013.01); *B01J 37/038* (2013.01); *B01J 37/04* (2013.01); *B01J 37/088* (2013.01); *B01J 37/16* (2013.01); *B01J 37/18* (2013.01); *C07C 2521/08* (2013.01); *C07C 2523/08* (2013.01); *C07C 2523/44* (2013.01); *C07C 2523/52* (2013.01); *C07C 2523/62* (2013.01); *C07C 2523/66* (2013.01)

(58) Field of Classification Search
None
See application file for complete search history.

(56) References Cited

U.S. PATENT DOCUMENTS

| | | | |
|---|---|---|---|
| 6,255,548 B1 * | 7/2001 | Didillon | B01J 23/62 208/134 |
| 2005/0048658 A1 * | 3/2005 | Johnson | B01J 23/50 436/37 |
| 2013/0102819 A1 * | 4/2013 | Szesni | B01J 31/0277 585/275 |

* cited by examiner

*Primary Examiner* — Philip Y Louie
(74) *Attorney, Agent, or Firm* — Troutman Pepper Hamilton Sanders LLP; Christopher C. Close, Jr.

(57) ABSTRACT

A process for preparing a catalyst for selective hydrogenation of acetylene to ethylene, comprises: mixing palladium, gallium, and gold sources, silica, and a solvent to form a suspension, which is then subjected to filtration and drying so as to obtain a catalyst precursor; subjecting the catalyst precursor obtained to a calcination treatment; and subjecting a calcinated product obtained to a reduction reaction in a reducing atmosphere so as to obtain the catalyst. The catalyst prepared according to this process exhibits a high stability and high catalytic performance, and has a large number of active sites uniformly distributed.

8 Claims, 4 Drawing Sheets

PROCESS FOR PREPARING CATALYST FOR SELECTIVE HYDROGENATION OF ACETYLENE TO ETHYLENE

FIELD OF THE INVENTION

The invention generally relates to the field of ethylene production, and particularly to a catalyst for selective hydrogenation of acetylene to ethylene, a process for making the catalyst as well as a process for the selective hydrogenation of acetylene to ethylene using the catalyst.

BACKGROUND OF THE INVENTION

Ethylene is an important petrochemical product and mainly used for producing polyethylene. However, the ethylene feed gas often contains a micro-amount (around 1%) of acetylene, which can poison a catalyst used in the ethylene polymerization reaction, resulting in a decrease in the quality of the polyethylene products. In industrial practice, acetylene is typically removed from the ethylene feed gas so as to lower its concentration to less than 5 ppm.

Currently, there are two main methods for removing acetylene from the ethylene feed gas: selective hydrogenation, and partial oxidation and steam reforming methods. As compared to the latter, the former is advantageous due to little pollution, low energy consumption, an excellent acetylene removal effect, and an increased ethylene yield. Catalysts now used industrially and widely in practice in the selective hydrogenation of acetylene to ethylene allow a high conversion of acetylene to be achieved, but provide a low selectivity of ethylene, which may adversely affect the subsequent polymerization reaction of ethylene. Moreover, these catalysts do not allow prompt desorption of the formed ethylene product from them during the hydrogenation reaction. This may induce excess hydrogenation to form ethane and thus a low selectivity of ethylene. Accordingly, it is desired to provide a catalyst for the selective hydrogenation of acetylene to ethylene, which can provide a high conversion of acetylene and a high selectivity of ethylene.

SUMMARY OF THE INVENTION

Objectives of the invention is to provide a catalyst for selective hydrogenation of acetylene to ethylene, a process for making the catalyst as well as a process for the selective hydrogenation of acetylene to ethylene using the catalyst. The catalyst according to the invention generally includes three metals as catalytically active components, with low amounts of precious metals, and can provide a high conversion of acetylene and a high selectivity of ethylene. Moreover, the catalyst according to the invention exhibits a high stability, a long service life, and a low production cost.

An objective of the invention is realized by a process for preparing a catalyst for selective hydrogenation of acetylene to ethylene, comprising steps of:

(a) mixing palladium, gallium, and gold sources, silica, and a solvent to form a suspension, which is then subjected to filtration and drying so as to obtain a catalyst precursor;

(b) subjecting the catalyst precursor of step (a) to a calcination treatment; and (c) subjecting a calcinated product of step (b) to a reduction reaction in a reducing atmosphere so as to obtain the catalyst.

The palladium source used in step (a) preferably comprises one of chloropalladic acid, palladium acetate, sodium tetrachloropalladate(II), palladium nitrate, palladium acetylacetonate, and ammonium tetrachloropalladate(II).

The gallium source used in step (a) preferably comprises one of gallium nitrate, gallium chloride acid, gallium ethoxide, gallium isopropoxide, gallium 2,4-pentanedionate, and triethylgallium.

The gold source used in step (a) preferably comprises one of chloroauric acid, gold acetate, gold potassium chloride, gold bromide, and gold acid chloride trihydrate.

A particle size of the silica used in step (a) is preferably in a range of 10 to 100 mesh.

The palladium, gallium, and gold sources and the silica may be mixed with a mass ratio of the palladium element:the gallium element: the gold element:the silica being preferably in a range of (0.05-0.8):(0.3-2):(0.1-0.4):100.

In step (b), the calcination treatment is preferably performed at a temperature of about 200 to 600° C. for about 1 to 6 hours.

Preferably, the reducing gas used in step (c) comprises one or more of hydrogen, methane, hydrogen sulfide, and ammonia gas.

The reduction reaction is preferably carried out at a temperature of about 100 to 600° C. for about 1 to 5 hours.

The invention also regards the catalyst prepared according to the above process of the invention.

The invention further regards a process for selective hydrogenation of acetylene to ethylene using the above catalyst of the invention.

One aspect of the invention regards a process for preparing a catalyst for selective hydrogenation of acetylene to ethylene, comprising mixing palladium, gallium, and gold sources, silica, and a solvent to form a suspension, which is then subjected to filtration and drying so as to obtain a catalyst precursor; subjecting the catalyst precursor to a calcination treatment; and subjecting a calcined product to a reduction reaction in a reducing atmosphere so as to obtain the catalyst. According to this aspect of the invention, palladium, gallium, and gold sources, and silica are employed as raw materials, and subjected to a calcination treatment and then a reduction reaction, causing the three metals to be interacted with each other and thus a trimetal structure to be formed which is stable in liquid form, and also causing the surface of the silica carrier to be uniformly and securely covered by the trimetal structure. This enables the three active metal components to be uniformly distributed on and firmly bonded onto the surface of the silica carrier. A catalyst, which exhibits a high stability and high catalytic performance and has a large number of active sites uniformly distributed, can be thus obtained. During the hydrogenation of acetylene to the ethylene product, electron structures of the three types of metal atoms at the active sites on the surface of the catalyst can interact with each other so that the acetylene adsorption ability of the active sites can be increased and their ethylene adsorption ability can be decreased. The likelihood of the side reaction of the hydrogenation of ethylene can thus be reduced. Therefore, the catalyst of the invention can provide a high conversion of acetylene and a high selectivity of ethylene. It was also found that the active metal components are partially oxidized during the catalytic reaction to form a self protecting oxide layer, which can suppress the hydrogenation of ethylene occurred on the surface of the catalyst and thus avoid the excess hydrogenation of acetylene to ethane. According to embodiments of the invention, by using the catalyst of the invention in the hydrogenation of acetylene to ethylene, the ethylene selectivity can be up to 99.2% and the acetylene conversion can be up to 99.4%. Moreover, the high catalytic performance of the catalyst according to the invention can be maintained for about 90 hours thanks to its high stability.

The process for preparing a catalyst for hydrogenation of acetylene to ethylene according to the invention is suitable for commercial production because of its simple process and mild reaction condition.

DETAILED DESCRIPTION

Figure 1:
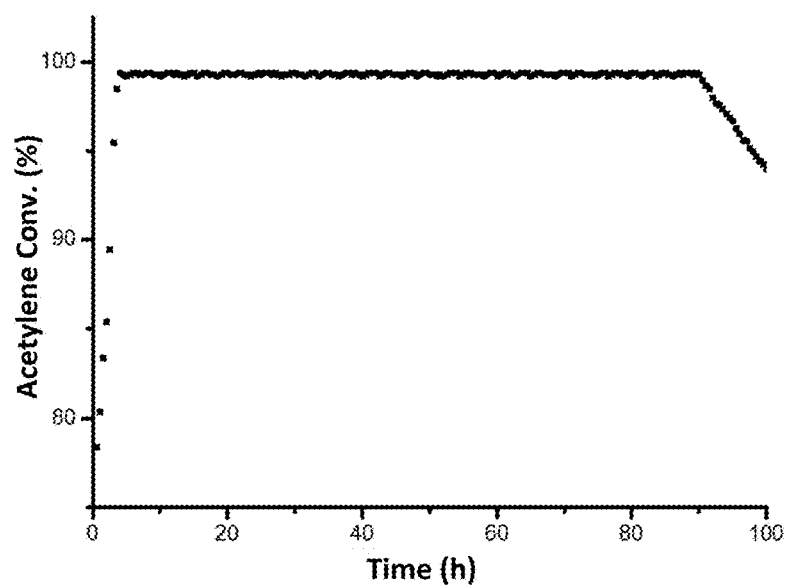
FIG. 1 is a graphic illustration of acetylene conversion over time, obtained in the case that a catalyst prepared in example 1 of the invention is used in the hydrogenation of acetylene to ethylene.

A first aspect of the invention provides a process for preparing a catalyst for selective hydrogenation of acetylene to ethylene, comprising steps of:

(a) mixing palladium, gallium, and gold sources, silica, and a solvent to form a suspension, which is then subjected to filtration and drying so as to obtain a catalyst precursor;

(b) subjecting the catalyst precursor of step (a) to a calcination treatment; and (c) subjecting a calcinated product of step (b) to a reduction reaction in a reducing atmosphere so as to obtain the catalyst.

According to the first aspect of the invention, palladium, gallium, and gold sources, silica, and a solvent are mixed to form a suspension. In an embodiment of the invention, the palladium source comprises one of chloropalladic acid, palladium acetate, sodium tetrachloropalladate(II), palladium nitrate, palladium acetylacetonate, and ammonium tetrachloropalladate(II). The origin of the palladium source is not particularly limited, and any commercial product known to those skilled in the art may be used, or it can be prepared according to any known method. The preparation of chloropalladic acid may comprise dissolving palladium chloride ($PdCl_2$) in concentrated hydrochloric acid to form a mixture, which is then diluted with deionized water to obtain the chloropalladic acid solution. A preferred concentration of the concentrated hydrochloric acid is 12 mol/L.

In an embodiment of the invention, the gallium source comprises one of gallium nitrate, gallium chloride acid, gallium ethoxide, gallium isopropoxide, gallium 2, 4-pentanedionate, and triethylgallium. The origin of the gallium source is not particularly limited, and any commercial product known to those skilled in the art may be used, or it can be prepared according to any known method. The preparation of gallium chloride acid may comprise dissolving gallium trichloride ($GaCl_3$) in concentrated hydrochloric acid to form a mixture, which is then diluted with deionized water to obtain the gallium chloride acid solution. A preferred concentration of the concentrated hydrochloric acid is 12 mol/L.

In an embodiment of the invention, the gold source comprises one of chloroauric acid, gold acetate, gold potassium chloride, gold bromide, and gold acid chloride trihydrate. In a particular embodiment, chloroauric acid is used as the gold source. The origin of chloroauric acid, gold acetate, gold potassium chloride, gold bromide, and gold acid chloride trihydrate is not particularly limited, and any commercial product known to those skilled in the art may be used.

The silica used in embodiments of the invention has an average particle size of about 10 to 100 mesh, preferably about 40 to 80 mesh. The origin of the silica is not particularly limited, and any commercial product known to those skilled in the art may be used. A control of the particle size of the silica within such a range is useful to provide uniform coverage of the three active metal components (i.e., palladium (Pd), gallium (Ga), and gold (Au)) on the surface of the silica carrier as well as to provide a firm bond between the components and the surface of the silica carrier.

In a particular embodiment, the solvent is deionized water. The origin of the solvent is not particularly limited, and any commercial product known to those skilled in the art may be used.

In embodiments of the invention, a ratio of the solvent volume to a total mass of the palladium, gallium, and gold sources is 7-13 mL: 1.5-5 mg, preferably 8-12 mL: 2-4 mg.

In an embodiment of the invention, mixing the palladium, gallium, and gold sources, silica, and the solvent comprises mixing each of the palladium, gallium, and gold sources with a portion of the solvent to prepare solutions of a palladium precursor, a gallium precursor, and a gold precursor, respectively; mixing the palladium, gallium, and gold precursor solutions together and with a reminder of the solvent to form a mixed solution; and mixing the mixed solution with silica to form the suspension.

The preparation of the palladium, gallium, and gold precursor solutions is not particularly limited, and any method known to those skilled in the art may be used. In a particular embodiment, the method of preparation comprises dissolving each of the palladium, gallium, and gold sources in a small amount of the solvent and then adding to each of the resultant solutions a reminder of the portion of the solvent to form the palladium, gallium, and gold precursor solutions, respectively. The palladium, gallium, and gold precursor solutions may each have a concentration of about 5 to 15 mg/mL, preferably about 8 to 12 mg/mL.

According to the embodiment of the invention, the palladium, gallium, and gold precursor solutions are then mixed together and with a reminder of the solvent to form a mixed solution. In a particular embodiment of the invention, the mixing is carried out under stirring for about 20 to 120 minutes, preferably about 30 to 60 minutes. The stirring speed is not particularly limited and a normal speed may be used.

According to the embodiment of the invention, the mixed solution is then mixed with silica to form the suspension. In a particular embodiment, the mixing is carried out under stirring for about 2 to 12 hours, preferably about 4 to 10 hours, further preferably about 6 hours. The stirring speed is not particularly limited and a normal speed may be used.

In embodiments of the invention, the palladium, gallium, and gold sources, and the silica are mixed with a mass ratio of the palladium element:the gallium element:the gold element:the silica being in a range of (0.05-0.8):(0.3-2):(0.1-0.4):100, preferably (0.2-0.6):(0.5-1): (0.15-0.3):100, further preferably 0.36:0.83:0.24:100. A control of such a ratio may be favorable to the interaction among the three types of metal atoms formed during the subsequent reduction reaction so as to form a trimetal structure, which is stable in liquid form and which allows for uniform coverage of the metal atoms on the silica surface as well as a firm bond between the atoms and the surface. This enables the catalyst obtained to exhibit a high stability and high catalytic performance and have a large number of active sites uniformly distributed.

According to the invention, the suspension is then subjected to filtration and drying so as to obtain a catalyst precursor. Filtration of the suspension is not particularly limited, and may be carried out in any suitable manner known to those skilled in the art. In some embodiments, the drying is carried out at a temperature of about 70 to 100° C., preferably about 80 to 90° C., for about 6 to 12 hours, preferably about 7 to 10 hours.

According to the invention, the catalyst precursor obtained is subjected to a calcination treatment to obtain a calcinated product. During the calcination, palladium, gallium, and gold precursors are pyrolyzed to form palladium oxide, gallium oxide, and gold, respectively, which are firmly supported on the silica surface. In some embodiments, the calcination treatment is carried out at a temperature of about 200 to 600° C., preferably about 300 to 500° C., for about 1 to 6 hours, preferably about 3 to 5 hours. A control of the calcination temperature and time within such ranges allows the catalyst precursor to be sufficiently calcinated and the calcinated product to have a suitable particle size and to be structured. The calcination treatment may be carried out in an air atmosphere.

According to the invention, the calcinated product is subjected to a reduction reaction in a reducing atmosphere so as to obtain the catalyst. During the reduction reaction, palladium and gallium oxides are reduced to palladium and gallium, respectively, both of which may interact with gold so that a trimetal structure, which is stable in liquid form, can be formed. This trimetal structure can be firmly bonded onto the silica surface, which allows for uniform coverage of the three active metal components on the silica surface and a firm bond between the components and the surface. So, a catalyst, which exhibits a high stability and high catalytic performance and has a large number of active sites uniformly distributed, can be obtained. In some embodiments, the reducing gas comprises one or more of hydrogen, methane, hydrogen sulfide, and ammonia gas. In the case that the reducing gas comprises two or more of these gases, the volume ratio thereof is not particularly limited. The origin of the hydrogen, methane, hydrogen sulfide, and ammonia gas is not particularly limited, and any commercial product known to those skilled in the art may be used.

In some embodiments, the reduction reaction is carried out at a temperature of about 100 to 600° C., preferably about 200 to 400° C., for about 1 to 5 hours, preferably about 2 to 4 hours. A control of the temperature and time of the reduction reaction within such ranges allows the calcinated product to be sufficiently reduced and the catalyst obtained to have a suitable particle size and to be structured.

The process for preparing a catalyst for selective hydrogenation of acetylene to ethylene, according to the first aspect of the invention, is suitable for commercial production because of its simple process and mild conditions. The catalyst prepared according to this process contains three types of active metal components with low amounts of precious metals. The catalyst can also provide a high acetylene conversion and a high ethylene selectivity, and exhibit a high stability, a long service life, and a low cost.

A second aspect of the invention provides a catalyst prepared by the process according to the first aspect of the invention, the catalyst comprising a silica carrier and a palladium-gallium-gold alloy supported on a surface of the silica carrier.

A third aspect of the invention provides a process for selective hydrogenation of acetylene to ethylene using the catalyst according to the second aspect of the invention, the process comprising:

introducing a mixed gas containing acetylene, hydrogen, and ethylene into a reactor charged with the catalyst to perform an addition reaction of hydrogen gas to acetylene to give the ethylene product.

According to the third aspect of the invention, a mixed gas containing acetylene, hydrogen, and ethylene is introduced into a reactor charged with the catalyst of the second aspect of the invention to perform an addition reaction of hydrogen gas to acetylene to give the ethylene product. The reactor where the addition reaction occurs is not particularly limited, and any suitable reactor known to those skilled in the art may be used. In a particular embodiment, the reactor is a fixed bed reactor.

With regard to the mixed gas, a molar ratio of acetylene:hydrogen:ethylene may be about 1:1-10: 60-120, preferably about 1:2:100. The mixed gas may be introduced into the reactor under a gas hourly space velocity of about 1200 to 36000 $h^{-1}$, preferably about 1800 to 10000 $h^{-1}$, further preferably about 2400 $h^{-1}$.

In some embodiments, the addition reaction is carried out at a temperature of about 30 to 210° C., preferably about 50 to 100° C., further preferably about 70° C., under a pressure of about 0.02 to 0.2 MPa, preferably about 0.03 to 0.10 MPa, further preferably about 0.05 MPa.

By conducting the selective hydrogenation of acetylene to ethylene using the catalyst according to the second aspect of the invention, it is possible to achieve both a high acetylene conversion and a high selectivity of the ethylene product. Moreover, its production cost can be reduced because the catalyst of the invention contains low amounts of precious metals and has a long service life.

The invention will now be described in more details with reference to particular examples. It will be understood that the following examples are intended to describe embodiments of the invention and are not intended to limit the invention in any way.

EXAMPLES

Example 1

(1) Preparation of chloropalladic acid, gallium chloride acid, and chloroauric acid solutions a. 1 g of $PdCl_2$ was dissolved in concentrated hydrochloric acid and transferred into a 100 mL volumetric flask, and then diluted to volume using deionized water so as to form the chloropalladic acid solution at a concentration of 10 mg/mL;

b. 1 g of $GaCl_3$ was dissolved in concentrated hydrochloric acid and transferred into a 100 mL volumetric flask, and then diluted to volume using deionized water so as to form the gallium chloride acid solution at a concentration of 10 mg/mL;

c. 1 g of chloroauric acid was dissolved in deionized water and transferred into a 100 mL volumetric flask, and then diluted to volume using deionized water so as to form the chloroauric acid solution at a concentration of 10 mg/mL.

(2) Preparation of catalyst for selective hydrogenation of acetylene to ethylene d. using a 1 mL pipetting gun, 0.835 mL of the above prepared chloropalladic acid solution, 2.52 mL of the above prepared gallium chloride acid solution, and 0.42 mL of the above prepared chloroauric acid solution were added into 6.225 mL of deionized water and stirred for 0.5 hour to form a mixed solution, which was then mixed with 1 g of 60 mesh silica under stirring for 6 hours and further subjected to filtration and vacuum drying at 80° C. for 8 hours, so as to form a catalyst precursor, wherein a mass ratio of the palladium element in the chloropalladic acid solution:the gallium element in the gallium chloride acid solution:the gold element in the chloroauric acid solution:the silica was 0.36:0.83:0.24:100;

e. the catalyst precursor formed in step (d) was calcined in air at 500° C. for 4 hours to give a calcined product;

f. the calcined product obtained in step (e) was subjected to a reduction reaction in a hydrogen atmosphere at 300° C. for 2 hours so as to obtain the catalyst for the selective hydrogenation of acetylene to ethylene.

Reaction Example 1

The catalyst prepared in example 1 was used in performing the selective hydrogenation of acetylene to ethylene.

A mixed gas containing acetylene, hydrogen, and ethylene with a molar ratio of 1:2:100 was introduced into a fixed bed reactor charged with the catalyst under a gas hourly space velocity of 2400 $h^{-1}$ to perform an addition reaction of hydrogen gas to acetylene at 70° C. under 0.05 MPa to give the ethylene product, the results thereof being given in table 1.

FIG. 1 is a graphic illustration of acetylene conversion over time in the reaction described in reaction example 1. As can be seen from FIG. 1, the acetylene conversion can be up to 99.4% and the catalytic performance of the catalyst can be maintained for around 90 hours.

Figure 7:
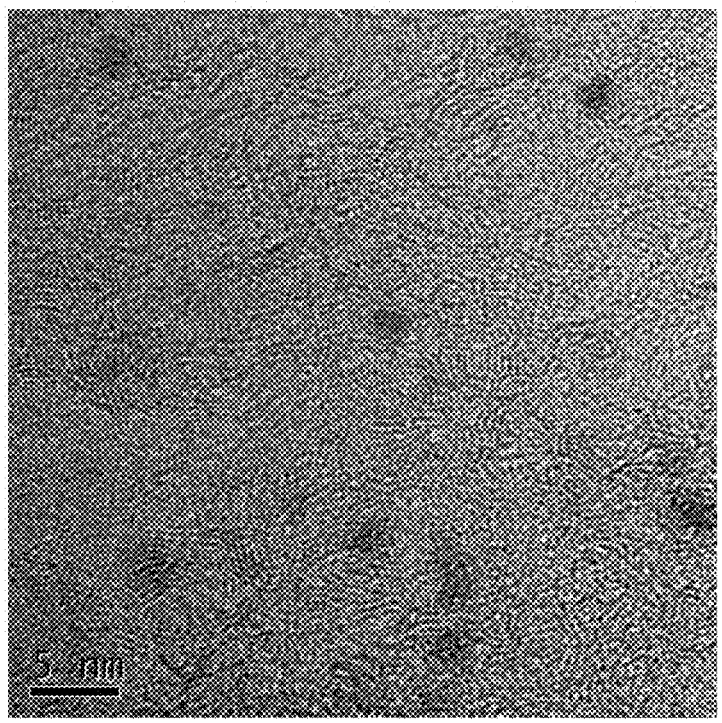
FIG. 7 is a transmission electron microscopy (TEM) image of the catalyst prepared in example 1 of the invention.

FIG. 7 is a TEM image of the catalyst prepared in example 1. As can be seen from FIG. 7, the catalyst particles have an uniform and small particle size.

Example 2

A catalyst was prepared in substantially the same manner as in example 1, except that 0.91 mL of the chloropalladic acid solution, 2.52 mL of the gallium chloride acid solution, and 0.42 mL of the chloroauric acid solution were mixed with 6.15 mL of deionized water, wherein a mass ratio of the palladium element in the chloropalladic acid solution:the gallium element in the gallium chloride acid solution:the gold element in the chloroauric acid solution:the silica was 0.39:0.83:0.24:100.

Example 3

A catalyst was prepared in substantially the same manner as in example 1, except that 0.67 mL of the chloropalladic acid solution, 2.52 mL of the gallium chloride acid solution, and 0.42 mL of the chloroauric acid solution were mixed with 6.39 mL of deionized water, wherein a mass ratio of the palladium element in the chloropalladic acid solution: the gallium element in the gallium chloride acid solution:the gold element in the chloroauric acid solution:the silica was 0.28:0.83:0.24:100.

Example 4

A catalyst was prepared in substantially the same manner as in example 1, except that 0.835 mL of the chloropalladic acid solution, 1.26 mL of the gallium chloride acid solution, and 0.21 mL of the chloroauric acid solution were mixed with 7.695 mL of deionized water, wherein a mass ratio of the palladium element in the chloropalladic acid solution: the gallium element in the gallium chloride acid solution:the gold element in the chloroauric acid solution:the silica was 0.36:0.41:0.12:100.

Reaction Examples 2-4

The catalysts prepared in examples 2-4 were used in reaction examples 2-4 respectively in performing the selective hydrogenation of acetylene to ethylene in the same manner as in the reaction example 1, the results thereof being given in table 1.

Figure 2:
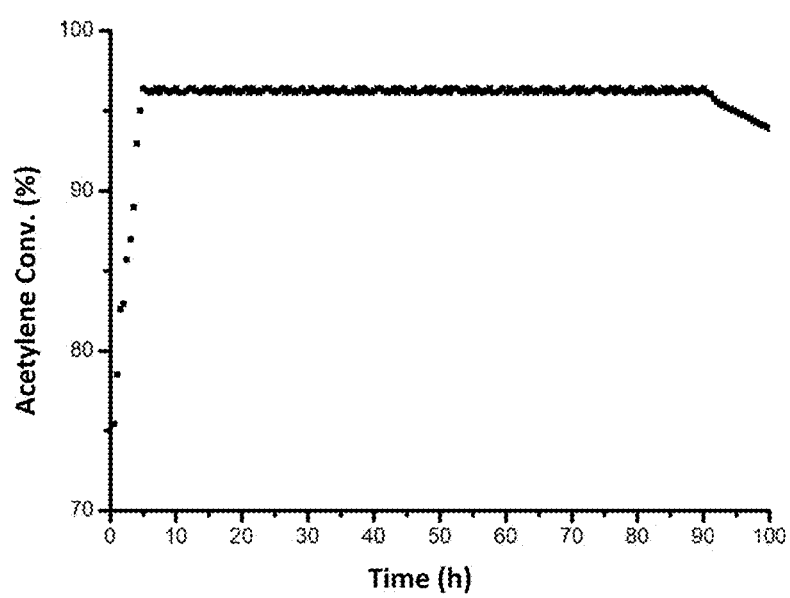
FIG. 2 is a graphic illustration of acetylene conversion over time, obtained in the case that a catalyst prepared in example 2 of the invention is used in the hydrogenation of acetylene to ethylene.

FIG. 2 is a graphic illustration of acetylene conversion over time in the reaction described in the reaction example 2. As can be seen from FIG. 2, the acetylene conversion can be up to 96.4% and the catalytic performance of the catalyst can be maintained for around 90 hours.

Figure 3:
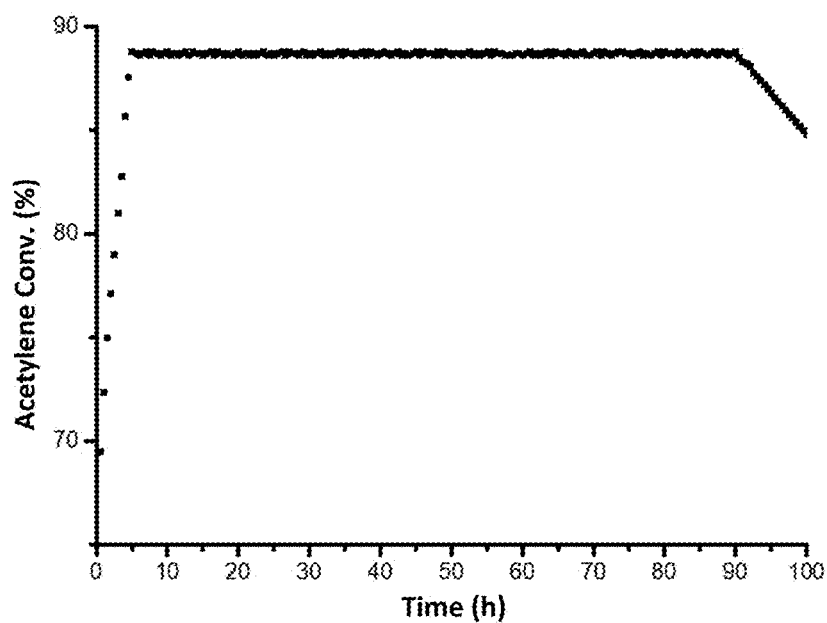
FIG. 3 is a graphic illustration of acetylene conversion over time, obtained in the case that a catalyst prepared in example 3 of the invention is used in the hydrogenation of acetylene to ethylene.

FIG. 3 is a graphic illustration of acetylene conversion over time in the reaction described in the reaction example 3. As can be seen from FIG. 3, the acetylene conversion can be up to 88.8% and the catalytic performance of the catalyst can be maintained for around 90 hours.

Figure 4:
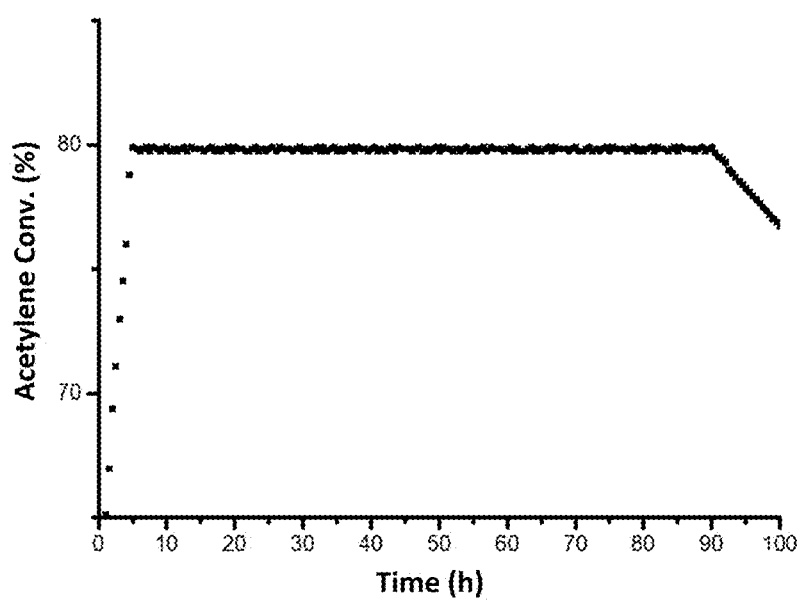
FIG. 4 is a graphic illustration of acetylene conversion over time, obtained in the case that a catalyst prepared in example 4 of the invention is used in the hydrogenation of acetylene to ethylene.

FIG. 4 is a graphic illustration of acetylene conversion over time in the reaction described in the reaction example 4. As can be seen from FIG. 4, the acetylene conversion can be up to 79.9% and the catalytic performance of the catalyst can be maintained for around 90 hours.

Comparative Example 1

A catalyst was prepared in substantially the same manner as in example 1, except that 0.835 mL of the chloropalladic acid solution and 2.52 mL of the gallium chloride acid solution were mixed with 6.645 mL of deionized water, wherein a mass ratio of the palladium element in the chloropalladic acid solution:the gallium element in the gallium chloride acid solution:the silica was 0.36:0.83:100. The catalyst obtained was used in performing the selective hydrogenation of acetylene to ethylene in the same manner as in the reaction example 1, the results thereof being given in table 1.

Figure 5:
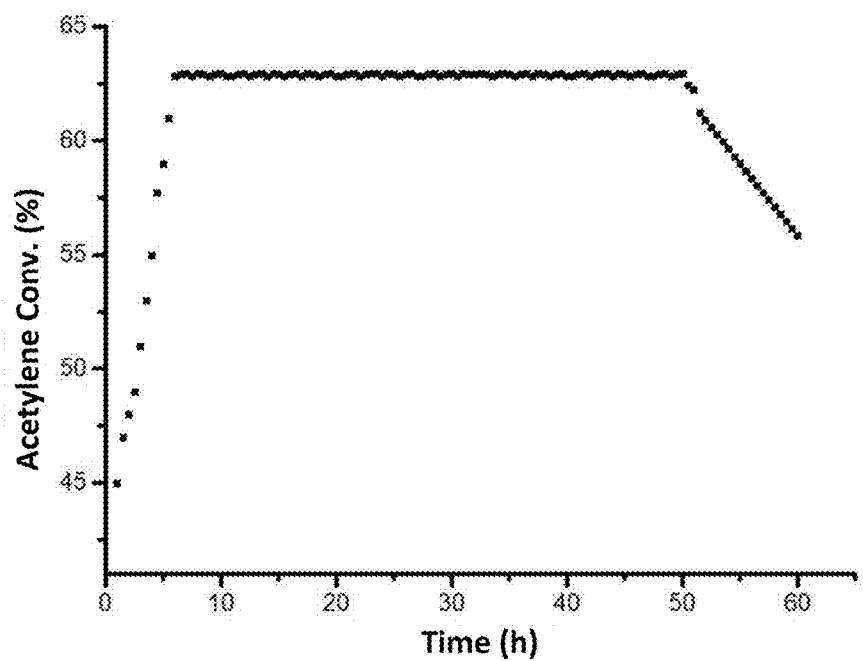
FIG. 5 is a graphic illustration of acetylene conversion over time, obtained in the case that a catalyst prepared in comparative example 1 is used in the hydrogenation of acetylene to ethylene.

FIG. 5 is a graphic illustration of acetylene conversion over time in the reaction described in the comparative example 1. As can be seen from FIG. 5, the acetylene conversion can be up to 62.8% and the catalytic performance of the catalyst can be maintained for around 50 hours.

Comparative Example 2

A catalyst was prepared in substantially the same manner as in example 1, except that 0.835 mL of the chloropalladic acid solution and 0.42 mL of the chloroauric acid solution were mixed with 8.745 mL of deionized water, wherein a mass ratio of the palladium element in the chloropalladic acid solution:the gold element in the chloroauric acid solution:the silica was 0.36:0.24:100. The catalyst obtained was used in performing the selective hydrogenation of acetylene to ethylene in the same manner as in the reaction example 1, the results thereof being given in table 1.

Figure 6:
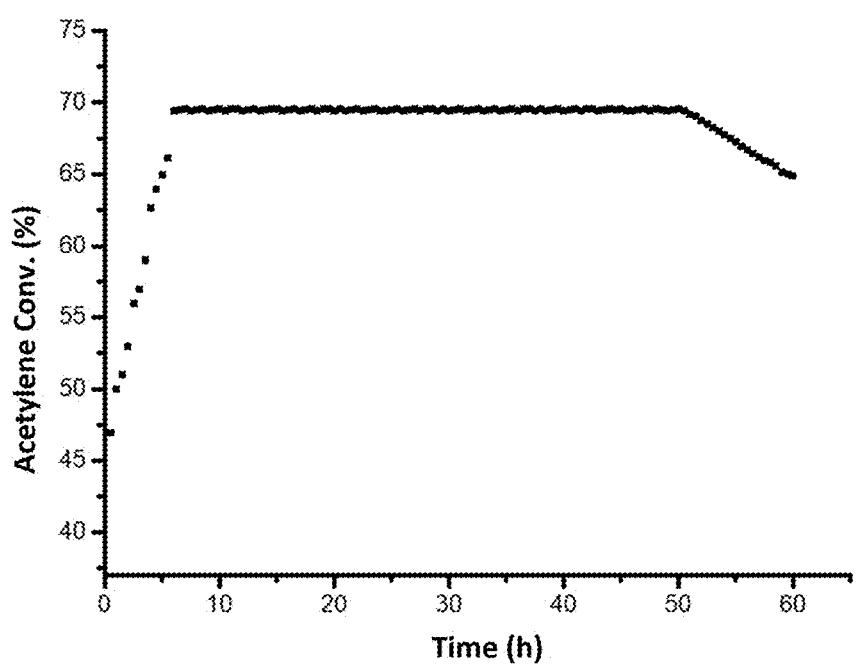
FIG. 6 is a graphic illustration of acetylene conversion over time, obtained in the case that a catalyst prepared in comparative example 2 is used in the hydrogenation of acetylene to ethylene.

FIG. 6 is a graphic illustration of acetylene conversion over time in the reaction described in the comparative example 2. As can be seen from FIG. 6, the acetylene conversion can be up to 69.5% and the catalytic performance of the catalyst can be maintained for around 50 hours.

TABLE 1

|  | Acetylene Conversion (%) | Ethylene Selectivity (%) |
|---|---|---|
| Reaction Example 1 | 99.4 | 99.2 |
| Reaction Example 2 | 96.4 | 93.4 |
| Reaction Example 3 | 88.8 | 90.7 |
| Reaction Example 4 | 79.9 | 81.5 |
| Comp. Example 1 | 62.8 | 49.7 |
| Comp. Example 2 | 69.5 | 55.6 |

As can be seen from table 1, by using the catalyst according to the invention, ethylene can be produced with a selectivity of up to 99.2%. Meanwhile, the acetylene conversion can be up to 99.4%. Further, the catalytic performance of the catalyst can be maintained for around 90 hours because of its high stability. Results of the reaction examples 1-4 show clear advantages over the comparative examples 1 and 2 as well as the prior art (with an ethylene selectivity being around 95% and a shorter catalyst run-time being around 48 hours).

While the invention has been described with reference to certain exemplary embodiments thereof, it will be understood by those skilled in the art that various changes and modifications of the embodiments may be made without departing from the spirit and the scope of the invention as defined by the following claims and their equivalents.

What is claimed is:

1. A process for preparing a catalyst for selective hydrogenation of acetylene to ethylene, comprising steps of:
    (a) mixing palladium, gallium, and gold sources, silica, and a solvent to form a suspension, which is then subjected to filtration and drying so as to obtain a catalyst precursor;
    (b) subjecting the catalyst precursor of step (a) to a calcination treatment; and
    (c) subjecting a calcinated product of step (b) to a reduction reaction in a reducing atmosphere so as to obtain the catalyst, wherein
    the gallium source used in said step (a) is gallium chloride acid,
    the gold source used in said step (a) is chloroauric acid,
    a particle size of the silica used in said step (a) is in a range of 10 to 100 mesh, and
    the palladium, gallium, and gold sources and the silica are mixed with a mass ratio of the palladium element:the gallium element:the gold element:the silica being in a range of (0.05-0.8):(0.3-2):(0.1-0.4):100.

2. The process according to claim 1, wherein the palladium source used in said step (a) comprises one of chloropalladic acid, palladium acetate, sodium tetrachloropalladate(II), palladium nitrate, palladium acetylacetonate, and ammonium tetrachloropalladate(II).

3. The process according to claim 1, wherein the calcination treatment in said step (b) is carried out at a temperature of about 200 to 600° C. for about 1 to 6 hours.

4. The process according to claim 1, wherein the reducing gas used in said step (c) comprises one or more of hydrogen, methane, hydrogen sulfide, and ammonia gas.

5. The process according to claim 1, wherein the reduction reaction in said step (c) is carried out at a temperature of about 100 to 600° C. for about 1 to 5 hours.

6. A catalyst for selective hydrogenation of acetylene to ethylene prepared according to the process of claim 1.

7. The catalyst according to claim 6, comprising:
    a silica carrier; and
    a palladium-gallium-gold alloy supported on a surface of the silica carrier.

8. A process for selective hydrogenation of acetylene to ethylene using the catalyst of claim 6, comprising:
    introducing a mixed gas containing acetylene, hydrogen, and ethylene into a reactor charged with the catalyst to perform an addition reaction of hydrogen gas to acetylene to give the ethylene product.

* * * * *